US009402532B2

(12) United States Patent
Smith et al.

(10) Patent No.: US 9,402,532 B2
(45) Date of Patent: Aug. 2, 2016

(54) OPTICAL OBTURATOR

(71) Applicant: Covidien LP, Mansfield, MA (US)

(72) Inventors: Robert C. Smith, Middlefield, CT (US); Gennady Kleyman, Brooklyn, NY (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 13/904,370

(22) Filed: May 29, 2013

(65) Prior Publication Data

US 2013/0345512 A1 Dec. 26, 2013

Related U.S. Application Data

(60) Provisional application No. 61/664,206, filed on Jun. 26, 2012.

(51) Int. Cl.
*A61B 1/00* (2006.01)
*A61B 17/34* (2006.01)
*A61B 1/12* (2006.01)
*A61B 17/00* (2006.01)

(52) U.S. Cl.
CPC .......... *A61B 1/00154* (2013.01); *A61B 17/3417* (2013.01); *A61B 17/3462* (2013.01); *A61B 2017/00907* (2013.01); *A61B 2017/347* (2013.01); *A61B 2017/3456* (2013.01)

(58) Field of Classification Search
CPC ........... A61B 17/3417; A61B 17/3438; A61B 2017/3441
USPC .................. 600/114, 204, 153–159; 264/1.1; 606/190; 604/167.01–167.06
See application file for complete search history.

(56) References Cited

U.S. PATENT DOCUMENTS 5,342,315 A   8/1994   Rowe et al.
6,315,714 B1  11/2001  Akiba
(Continued)

FOREIGN PATENT DOCUMENTS

AU   2011 221 382      9/2011
EP    1 262 150 A2    12/2002
(Continued)

OTHER PUBLICATIONS

European Search Report EP 13 17 3485 dated Oct. 7, 2013.
Extended European Search Report dated Oct. 4, 2013 for EP 13 17 2212.

*Primary Examiner* — Anhtuan T Nguyen
*Assistant Examiner* — Timothy J Neal

(57) ABSTRACT

An optical obturator for penetrating tissue and being at least partially positionable within a cannula assembly. The obturator may include an obturator housing at a proximal end of the obturator and may configured to be grasped by a user. The obturator housing may define an opening for receiving an endoscope, the obturator housing including an endoscope retention mechanism adapted for securing and stabilizing an endoscope inserted therethrough. The obturator housing may also include at least one attachment mechanism for enabling selective attachment and detachment of the obturator housing to the cannula assembly. The obturator may also include an obturator shaft integrally formed with the obturator housing. The obturator shaft may define a hollow interior configured to receive the endoscope inserted through the opening. A penetrating member is disposed at the distal end of the obturator shaft. The obturator may be formed as a single component, preferably from transparent material.

13 Claims, 7 Drawing Sheets

(56) References Cited

U.S. PATENT DOCUMENTS

| | | | |
|---|---|---|---|
| 7,303,548 B2 * | 12/2007 | Rhad | A61M 5/3273 604/164.08 |
| 7,597,701 B2 | 10/2009 | Hueil et al. | |
| 2005/0288622 A1 | 12/2005 | Albrecht et al. | |
| 2010/0081988 A1 | 4/2010 | Kahle et al. | |
| 2010/0094228 A1 | 4/2010 | Bettuchi et al. | |
| 2012/0089094 A1 | 4/2012 | Franer et al. | |

FOREIGN PATENT DOCUMENTS

| | | |
|---|---|---|
| EP | 2 138 111 | 12/2009 |
| EP | 2 430 992 | 3/2012 |
| WO | WO 2005/032348 | 4/2005 |

* cited by examiner

OPTICAL OBTURATOR

CROSS REFERENCE TO RELATED APPLICATION

The present application claims the benefit of and priority to U.S. Provisional Application Ser. No. 61/664,206, filed on Jun. 26, 2012, the entire contents of which are incorporated herein by reference.

BACKGROUND

1. Technical Field

The present disclosure relates to an obturator. More particularly, the present disclosure relates to an optical obturator formed as a single component.

2. Background of Related Art

Minimally invasive procedures are continually increasing in number and variation. Forming a relatively small diameter, temporary pathway to the surgical site is a key feature of most minimally invasive surgical procedures. The most common method of providing such a pathway is by inserting a trocar assembly through the skin. Common trocar assemblies generally include an obturator for penetrating the skin and a cannula assembly for providing a sealed passageway for insertion of surgical instruments into a body cavity. In many procedures, the trocar assembly is inserted into a body cavity of a patient and the body cavity is insufflated to provide a working space. Upon removal of the obturator, the cannula assembly is utilized to provide the necessary pathway to the surgical site while minimizing leakage of insufflation gases. The obturator may include a safety shield which protects against unintentional puncturing by a sharpened tip of the obturator.

Conventional obturator assemblies are typically complex, with various different components being employed in order to provide the desired functionality.

SUMMARY

The present invention, according to various embodiments thereof, is directed to an optical obturator for penetrating tissue and being at least partially positionable within a cannula assembly. In an embodiment, the obturator comprises an obturator housing at a proximal end of the obturator and configured to be grasped by a user. The obturator housing may define an opening for receiving an endoscope. The obturator housing may include an endoscope retention mechanism adapted for securing and stabilizing an endoscope inserted therethrough. At least a portion of the endoscope retention mechanism may be integrally formed with the obturator housing. The obturator housing may further include at least one attachment mechanism for enabling selective attachment and detachment of the obturator housing to the cannula assembly. The at least one attachment mechanism may be integrally formed with the obturator housing. The obturator may also comprise an obturator shaft integrally formed with the obturator housing and defining a longitudinal axis. The obturator shaft may define proximal and distal ends. The obturator shaft may define a hollow interior in communication with the opening of the obturator housing and may be configured to receive the endoscope inserted through the opening. Also, the obturator may comprise a penetrating member at the distal end of the obturator shaft. The penetrating member may be integrally formed with the obturator shaft.

In an embodiment, the endoscope retention mechanism may include a slot defined by one of the obturator shaft and the opening of the obturator housing. The slot may be configured for receiving an endoscope engagement structure. The endoscope engagement structure may extend radially inwardly into the opening of the obturator housing. The endoscope engagement structure may include an o-ring that directly engages the endoscope. The o-ring may be resilient, such that an endoscope inserted into the opening radially displaces the o-ring from a resting position of the o-ring. In such an arrangement, the o-ring may provide a radial force on the endoscope inserted into the opening so as to help maintain the endoscope within the hollow interior of the obturator shaft.

In various embodiments, the at least one attachment mechanism may be a latch mechanism. For example, the latch mechanism may include a pair of radially displaceable legs disposed on opposed sides of the obturator housing, each leg having a tooth at its distal end. Displacing the legs radially inwardly may enable selective attachment and detachment of the teeth with respective corresponding openings of the cannula assembly.

In various embodiments, the penetrating member is bladeless. Advantageously, the entire obturator is molded from light transmissible material.

In addition, the present invention, according to various embodiments thereof, may be directed to a trocar assembly for penetrating tissue. The trocar assembly may comprise: a cannula assembly including a cannula housing and a cannula sleeve extending distally from the cannula housing; and an optical obturator for penetrating tissue and being at least partially positionable within a cannula assembly, the obturator comprising: an obturator housing at a proximal end of the obturator, the obturator housing having an outer surface that is gripped by a hand of a user, the obturator housing defining an opening for receiving an endoscope, the obturator housing including an endoscope retention mechanism adapted for securing and stabilizing an endoscope inserted therethrough, the obturator housing further including at least one attachment mechanism for enabling selective attachment and detachment of the obturator housing to the cannula assembly, the obturator further comprising an obturator shaft defining a longitudinal axis, and proximal and distal ends, the obturator shaft defining a hollow interior in communication with the opening of the obturator housing and configured to receive the endoscope inserted through the opening; the obturator further comprising a penetrating member at the distal end of the obturator shaft, and wherein the entire obturator is integrally formed as a single molded component.

In various embodiments, the endoscope retention mechanism may include a finger structure that extends radially inwardly into the opening of the obturator housing. The endoscope retention mechanism may include a slot for receiving an o-ring. The o-ring may extend radially inwardly into one of the opening and the hollow interior of the obturator shaft. The o-ring may be configured such that, when an endoscope is inserted, the endoscope radially displaces the o-ring. In such an arrangement, the o-ring may provide a radially inward force on the endoscope so as to help maintain the endoscope within the hollow interior of the obturator shaft.

In various embodiments, the at least one attachment mechanism is a latch mechanism. For example, the latch mechanism may include a pair of radially displaceable legs disposed on opposed sides of the obturator housing. Each leg may have a tooth at its distal end. Displacing the legs radially inwardly may enable selective attachment and detachment of the teeth with corresponding openings of the cannula assembly.

In various embodiments, the penetrating member is bladeless. The penetrating member may instead be bladed, e.g., having sharp edges for cutting through tissue. Advantageously, the entire obturator may be molded from light transmissible material.

In addition, the present invention, according to various embodiments thereof, may be directed to a method of manufacturing an optical obturator for use with a cannula assembly in penetrating tissue. The method may comprise the step of providing an injection mold including a mold cavity. The mold cavity may have a surface for defining at least portions of an optical obturator, including a portion of a grippable outer surface of an obturator housing at a proximal end of the obturator, a portion of an attachment mechanism for enabling selective attachment and detachment of the obturator housing to the cannula assembly, a portion of an obturator shaft and a portion of a penetrating member at the distal end of the obturator shaft. The method may also comprise the step of providing a core pin positionable within the mold cavity, the core pin defining at least a portion of an opening in the obturator housing, a hollow interior of the obturator shaft and a hollow interior of the penetrating member, such that the opening and the hollow interiors are in communication with each other. The method may comprise the step of injecting a polymeric material between the mold cavity and the core pin so as to form the obturator.

In various embodiments, the method of manufacturing is such that the surface of the mold cavity also defines at least a portion of an endoscope retention mechanism. For example, the endoscope retention mechanism may include a finger structure that extends radially inwardly into the opening of the obturator housing. Alternatively, the endoscope retention mechanism may include a slot, and the method may further comprise the step of arranging an o-ring in the slot. By doing so, the o-ring may extend radially inwardly into one of the opening and the hollow interior of the obturator shaft.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

Figure 1:
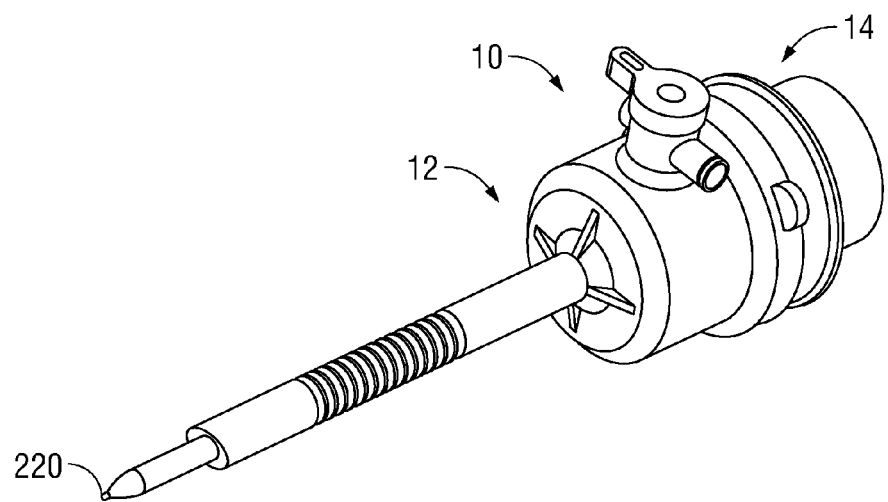
FIG. 1 is a perspective view of a trocar assembly including an obturator and a cannula assembly, in accordance with an example embodiment of the present invention.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Embodiments of the presently disclosed apparatus will now be described in detail with reference to the drawings, in which like reference numerals designate identical or corresponding elements in each of the several views. As used herein, the term "distal" refers to that portion of the tool, or component thereof, which is further from the user while the term "proximal" refers to that portion of the tool or component thereof which is closer to the user.

Figure 2:
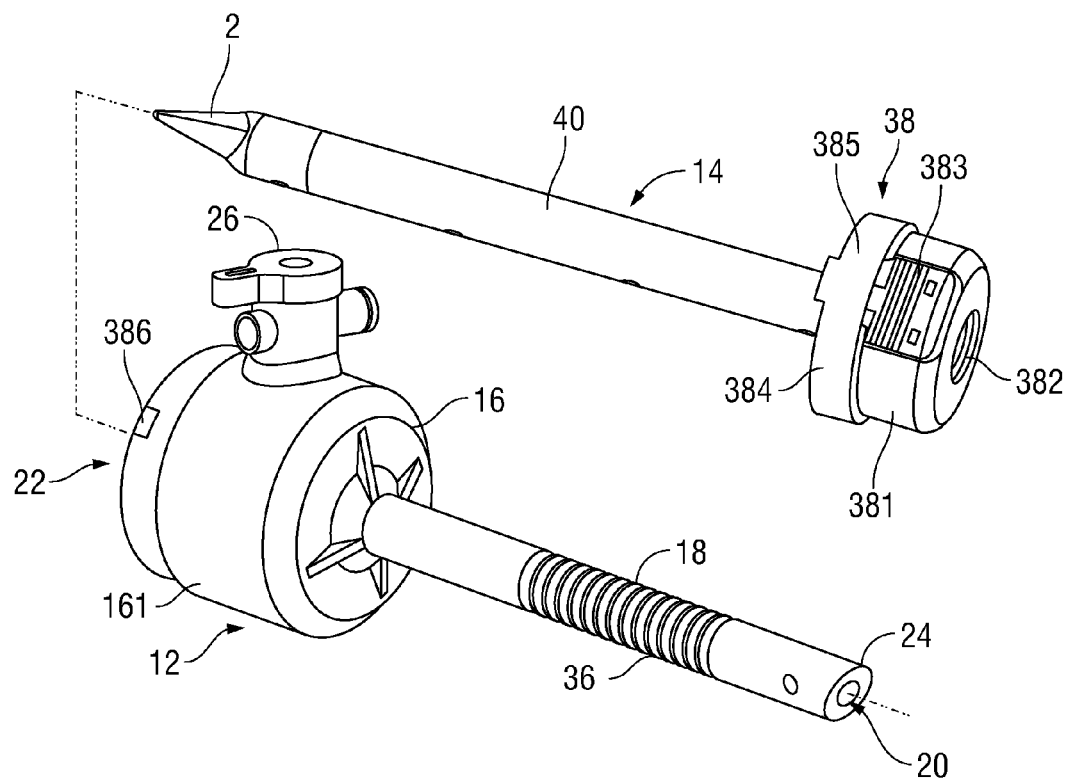
FIG. 2 is a perspective view of the trocar assembly of FIG. 1 illustrating the obturator separated from the cannula assembly, in accordance with the example embodiment of FIG. 1.
Figure 3A:
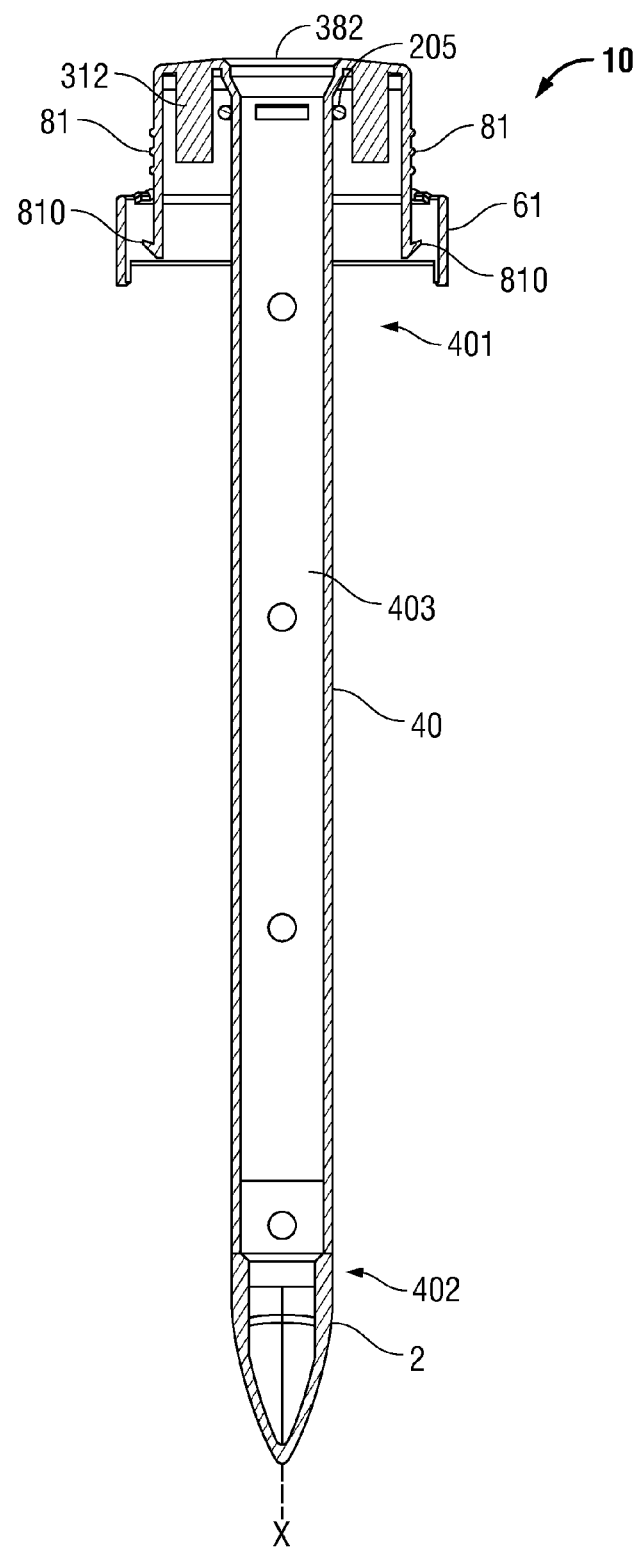
FIG. 3A is a side cross-sectional view of the obturator, in accordance with an example embodiment of the present invention.
Figure 3B:
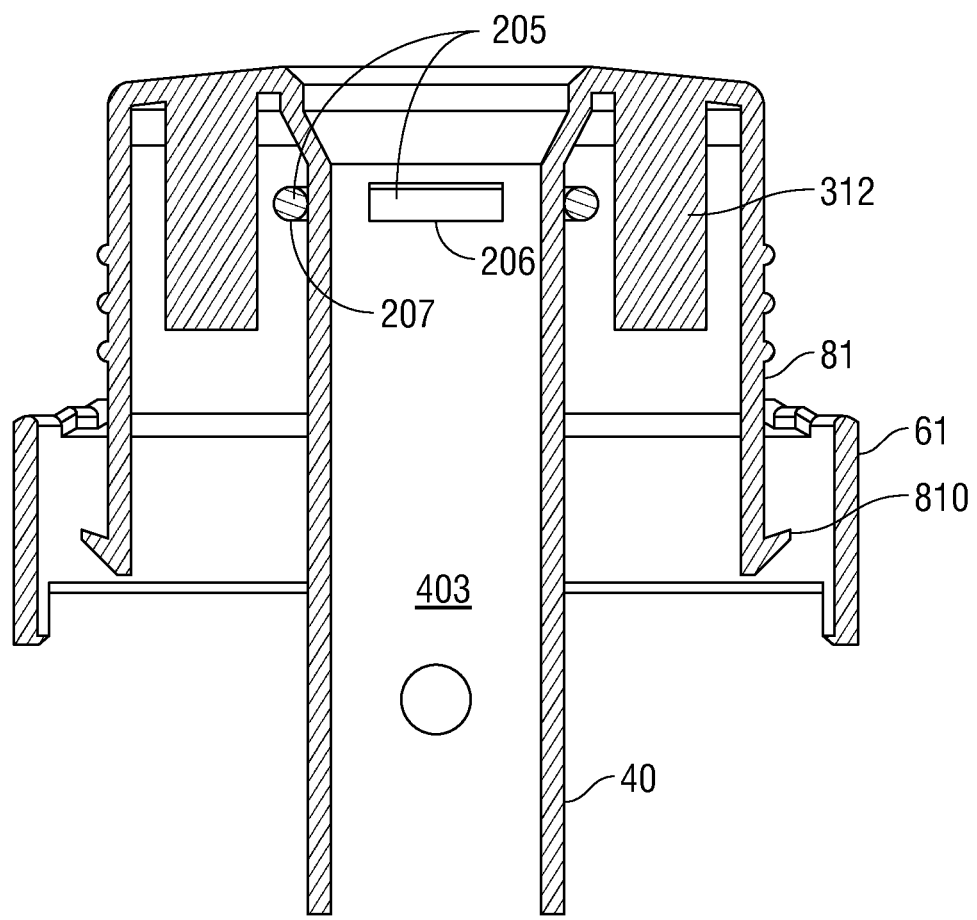
FIG. 3B is a side cross-sectional view of the obturator, in accordance with the example embodiment of FIG. 3A, showing additional details of the obturator housing.
Figure 4:
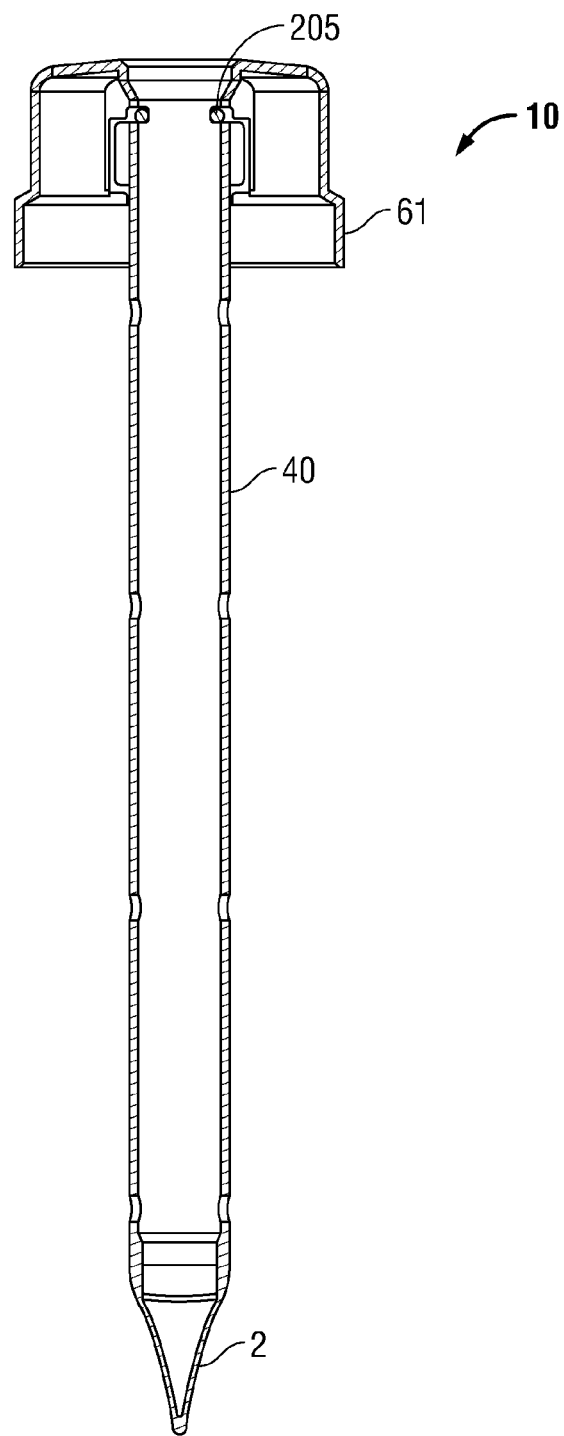
FIG. 4 is a front cross-sectional view of the obturator, in accordance with the example embodiment of FIG. 1.
Figure 5:
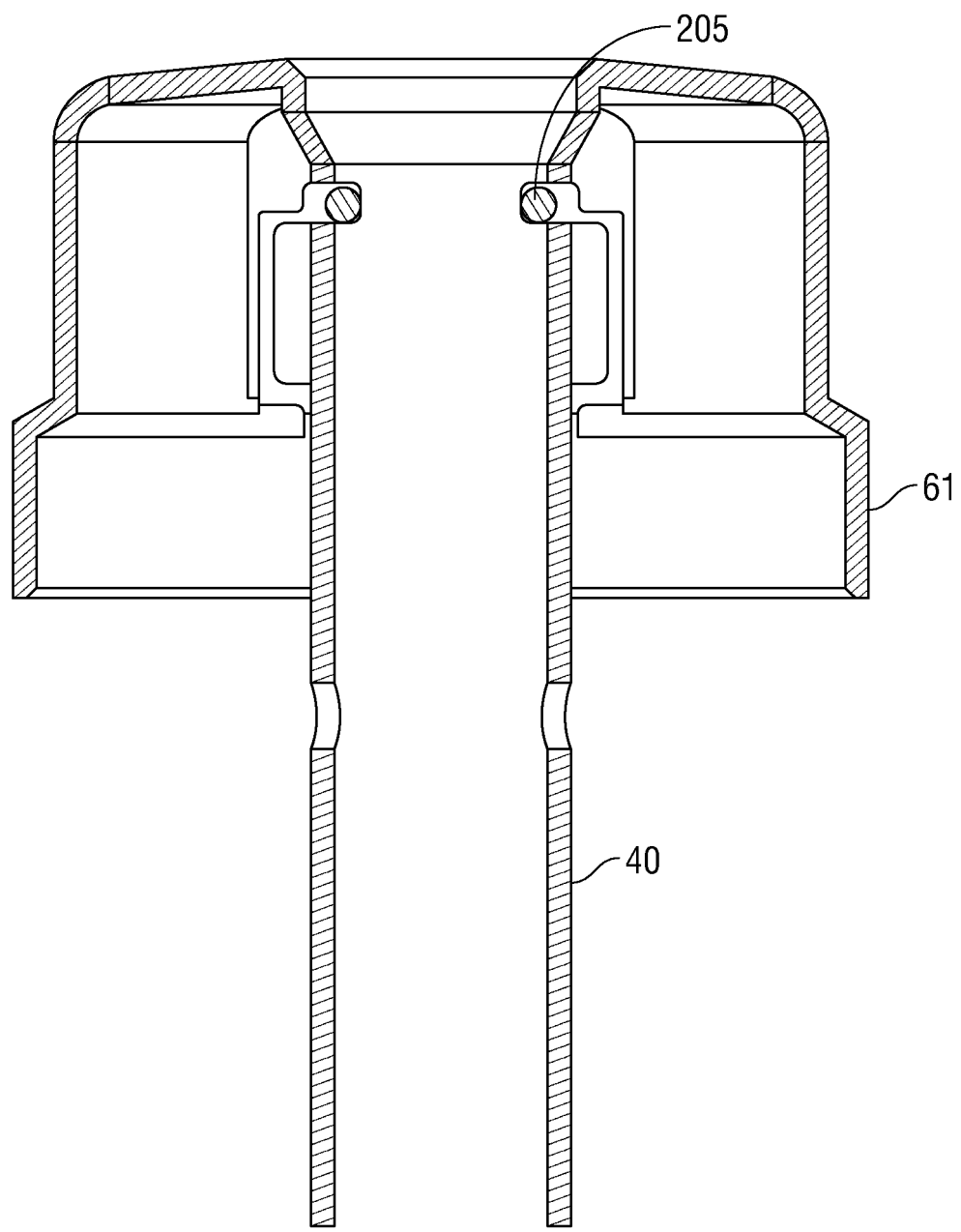
FIG. 5 is a front cross-sectional view of the obturator, in accordance with the example embodiment of FIG. 4, showing additional details of the obturator housing.
Figure 6:
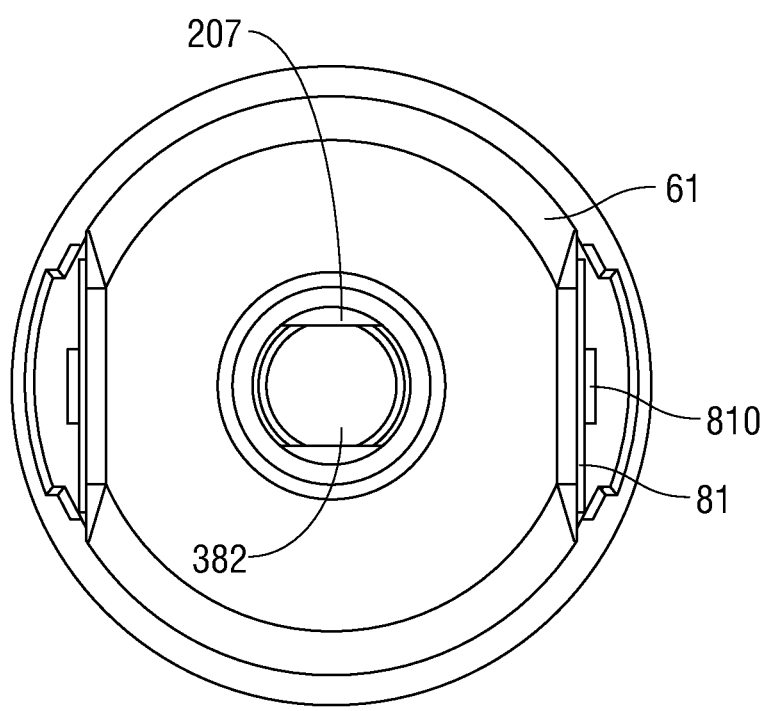
FIG. 6 is a top view of the obturator housing, in accordance with the example embodiment of FIG. 3A.
Figure 7:
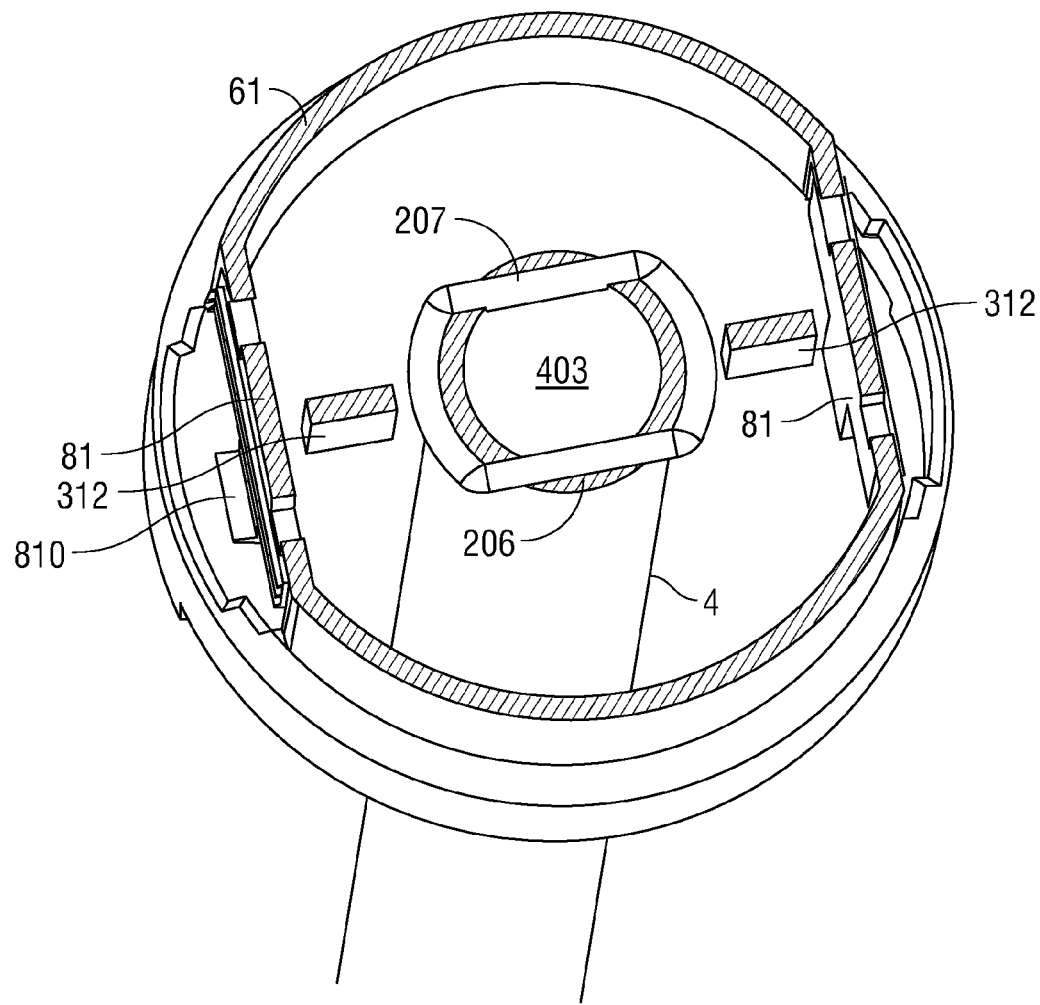
FIG. 7 is a perspective view of the obturator housing of FIG. 3A, shown in cross-section immediately proximal to an o-ring.

Referring to FIGS. 1 and 2, there is disclosed a trocar assembly 10 including a cannula assembly 12 and an obturator 14 positioned through cannula assembly 12. Cannula assembly 12 provides an access port for various surgical instruments into the body as well as a conduit for a source of insufflation fluid to insufflate the body to create a working cavity.

With reference to FIG. 2, cannula assembly 12 includes a cannula housing 16, including a seal structure (not shown), and elongate cannula sleeve 18 extending distally from cannula housing 16. Cannula housing 16 and cannula sleeve 18 define a throughbore 20, which extends from a proximal end 22 of cannula housing 16 to a distal end 24 of cannula sleeve 18. A valve 26 may be provided on cannula housing 16 to receive a source of insufflation fluid for passage into the body of a patient. The cannula sleeve 18 may also include a plurality of ribs 36. The plurality of ribs 36 may be a plurality of protrusions or a plurality of recesses.

With reference to FIG. 2, obturator 14 generally includes an obturator housing 38 and an elongate member 40 extending distally therefrom. Advantageously, the obturator 14 is a one-piece optical obturator, although it is contemplated that the obturator 14 may be formed of several different components that are attached together, e.g., by over-molding, two-shot molding, snap-fit, etc. The obturator 14 is configured for penetrating tissue and, as shown, may be at least partially positionable within a cannula assembly 12.

The obturator housing 38 is located at a proximal end of the obturator 14. The obturator housing 38 includes an outer surface 381 that is configured to be grasped by a user. The obturator housing 38 defines an opening 382 for receiving an endoscope. In addition, the obturator housing 38 includes an endoscope retention mechanism, an embodiment of which is shown in, e.g., FIGS. 3A through 7, discussed further below. The endoscope retention mechanism is adapted for securing and stabilizing an endoscope inserted therethrough.

The obturator housing 38 may also include at least one attachment mechanism 383 for enabling selective attachment and detachment of the obturator housing 38 to the cannula assembly 12. Advantageously, the endoscope retention mechanism and the at least one attachment mechanism 383 are integrally formed with the obturator housing as a single molded unit. Alternatively, the endoscope retention mechanism may include some components that are integrally formed with the obturator housing as a single molded unit, and an additional components or components that are not integrally formed with the obturator housing as a single molded unit, as will be explained in further detail below.

The obturator 14 also includes an obturator shaft 40 in the form of an elongate member. The obturator shaft 40 may be integrally formed with the obturator housing 38. The obturator shaft 40 may define a longitudinal axis x, and may further include a proximal end 401 and a distal end 402. The obturator shaft 40 may define a hollow interior 403 in communication with the opening 382 of the obturator housing 38. The hollow interior 403 may be configured to receive an endoscope (not shown) inserted through the opening 382.

The obturator 14 may also include a penetrating member 2 located at the distal end 402 of the obturator shaft 40. Advantageously, the penetrating member 2 may be integrally formed with the obturator shaft 40. The penetrating member 2 may have any one of a variety of different geometrical shapes suitable for penetrating tissue, e.g, conical, pyramidal, dolphin-nosed or otherwise tapered. The penetrating member 2 may have sharp edges so as to cut through tissue, or may instead be bladeless, allowing for dissection between tissue layers without cutting through the tissue.

Referring to FIGS. 3A through 7, additional details of an example embodiment of the obturator housing, having at least one attachment mechanism 383, is shown. As set forth above, at least one attachment mechanism 383 is configured for enabling selective attachment and detachment of the obturator housing 38 to the cannula assembly 12. In the embodiment shown, the at least one attachment mechanism 383 includes a latch mechanism, and specifically a latch mechanism that includes a pair of radially displaceable legs 81 disposed on opposed sides of the obturator housing 38. Each one of the pair of radially displaceable legs 81 has a tooth 810 at its distal end. In this configuration, displacing the legs 81 radially inwardly enables selective attachment and detachment of the teeth 810 with respective corresponding openings (not shown) of the cannula assembly 12. This selective attachment and detachment of the teeth 810 of legs 81 with respective corresponding openings of the cannula assembly 12 enables a user to attach the obturator 14 relative to the cannula assembly 12 when desirable, e.g., when the two components are collectively being inserted through tissue, while still enabling the user to detach the two components when the obturator 14 has penetrated tissue and when it is desirable for the cannula assembly to directly receive an instrument, e.g., an endoscope. The obturator housing 38 may also include a ring 61 that protects the legs 81 and that directly engages the housing 16 of the cannula assembly 12, e.g., by providing an outer surface 384 (see, e.g., FIG. 2) that mates with a radially outer surface 161 of the cannula assembly 12. FIG. 2 also illustrates that the ring 61 may include a protuberance 385 that mates with a corresponding recess 386 of cannula assembly so as to align these components relative to each other when attached by a user. Still further, the obturator housing 38 may include structure, e.g., ribs 312, that function to prevent the legs 81 from being moved too far in a radially inwardly direction. These ribs 312 may improve the reliability of the obturator housing 38 by decreasing the likelihood that a user will inadvertently move the legs 81 too far in a radially inwardly direction and/or improve the ability of the legs to align with the corresponding openings in the cannula assembly 12. As shown, the at least one attachment mechanism 383, e.g., legs 81 and the associated structure, may be integrally formed with the obturator housing 38 as a single molded unit.

Additional details of an example embodiment of the obturator housing 38 having an endoscope retention mechanism is shown. As set forth above, the endoscope retention mechanism may be adapted for securing and stabilizing an endoscope inserted therethrough. In an embodiment, the endoscope retention mechanism may include a finger or collet-type structure that extends radially inwardly into the opening 382 of the obturator housing 38 and that is molded as a single integral component with the obturator housing 38.

Alternatively, and referring specifically to FIGS. 3A through 7, there is shown additional details of an example embodiment of the obturator housing 38 having an endoscope retention mechanism 205. In this embodiment, the endoscope retention mechanism 205 includes a slot or slots 206 that extend through the wall of the obturator shaft 40. The slot or slots 206 are configured to receive a resilient structure, e.g., an o-ring 207. The resilient structure, e.g., the o-ring 207, may extend radially inwardly through the slot or slots 206 such that at least a portion of the resilient structure, e.g., o-ring 207, is positioned within one or both of the opening 382 of the obturator housing 38 and the hollow interior 403 of the obturator shaft 40.

Advantageously, the o-ring 207 is configured such that, when an endoscope is inserted through the opening 382 and into the hollow interior 403 of the obturator shaft 40, the endoscope radially displaces the o-ring 207, thereby causing the o-ring 207 to provide a radially inward force on the endoscope. This radially inward force on the endoscope enables the o-ring to help maintain the endoscope within the hollow interior 403 of the obturator shaft 40.

As set forth above, the penetrating member 2 may be bladeless, so as to provide for dissection through tissue planes/layers. Alternatively, the penetrating member 2 may have sharp edges so as to cut through tissue. Penetrating member 2 may be tapered, conical, pyramidal, dolphin-nosed (as explained above), frusto-conical and/or any other configuration suitable for passing through tissue. In various embodiments, penetrating member 2 may, e.g., a dolphin-nose configuration, with a rounded distal tip or nub 220 (as shown, e.g., in FIG. 1) to facilitate initial penetration between tissue layers. Penetrating member 2 may be substantially hollow to receive the distal end of an endoscope (not shown). Penetrating member 2 may be fabricated from any suitable plastic or polymeric material, e.g., polycarbonate, and advantageously is transparent or translucent to enable visualization therethrough.

The obturator 14 may be formed from a polymeric material such as polycarbonate or polystyrene. Advantageously, obturator 14 may be transparent throughout its entire length. Alternatively, only penetrating member 2, or even certain portions of the penetrating member 2, may be transparent or translucent. Also, certain portions of the obturator 14, e.g., the obturator housing 38, may be frosted or otherwise knurled, so as to provide an improved gripping surface.

The present invention, according to various embodiments thereof, may provide certain advantages as compared to conventional optical obturator assemblies. For example, conventional obturator assemblies are typically made of several different components that are either welded or snapped together at the time of assembly. Several components are typically required because conventional optical obturators rely on each one of the several components to provide some aspect of the desired functionality.

For example, conventional optical obturators often have an obturator shaft that is a separate component from the distal end, since it may be considered unnecessary for any structure other than the distal tip to be clear (since the distal tip of the endoscope is typically located at or adjacent to the distal end of the obturator when the endoscope is locked in place within the obturator shaft). In addition, conventional optical obturators often have separate and complex endoscope locking mechanisms for retaining an endoscope within the obturator shaft. For example, conventional obturator assemblies often include a camming mechanism which a user may selectively rotate in order to lock an endoscope within the obturator. Alternatively, other conventional obturator assemblies may include snap-fitted collet connections that attache to a proximal end of the obturator housing. Still further, conventional optical obturators often include separate and complex latching mechanisms for attaching the obturator to the cannula assembly. Also, conventional optical obturators often include separate obturator housing components for surrounding and protecting the various other mechanisms (e.g., the endoscope locking mechanisms, the latching mechanisms, etc.) and for providing an outer surface that a user may grip. All of these separate components are typically separately molded, requiring separate manufacturing molds, and are later assembled at the time of manufacture. Thus, the cost of manufacturing these types of conventional optical obturators is relatively expensive, due to the numerous different manufacturing molds required to be used, the separate handling of these separate components, the time and labor required to assemble them, etc.

By integrating all of these components into a single molded component, the optical obturator of the present invention, in accordance with various embodiments thereof, may significantly reduce the cost and complexity associated with manufacturing the device. Instead of requiring the design, purchase and use of separate molds for each one of numerous components, the optical obturator of the present invention, in accordance with various embodiments thereof, may be made using a single manufacturing mold. Only a single component, e.g., the entire obturator, is required to be handled (e.g., purchased, tracked, counted, stored, etc.), rather than needing to perform each one of these handling tasks, and often many more tasks, for each one of numerous separate components. Lastly, whereas conventional optical obturators require the costs of assembling the various separate components together—such costs which may include labor costs, the cost of manufacturing lines including welding stations, the costs of validating the fit between the various components, etc.—the optical obturator of the present invention, in accordance with various embodiments thereof, requires no assembly and thus may have little or even no assembly costs associated with it. As a result of these various aspects, the optical obturator of the present invention, in accordance with various embodiments thereof, may be manufactured with less complexity and at substantially lower cost than conventional optical obturators.

Even the embodiment described herein that includes an o-ring 207 as a component of the endoscope retention mechanism provides a significant advantage in manufacturing complexity and cost as compared to conventional optical obturators. The o-ring may be an off-the-shelf component, costing virtually nothing, and which is assembled with the obturator in a very simple step of rolling the o-ring up the outer surface of the obturator shaft 40 until the o-ring 207 drops into the corresponding slot or slots 206. Such a step, even for this example embodiment, requires no additional equipment, e.g., no welding or snap-fit equipment, no training for assembling, etc.

In addition, the optical obturator of the present invention, in accordance with various embodiments thereof, may provide better functionality than conventional optical obturators that are made of several different components that are either welded or snapped together at the time of assembly. For example, a conventional optical obturator that has an opaque obturator shaft, with a transparent or translucent distal tip located at the distal end thereof, only provides visualization of tissue if the endoscope is fully inserted through the hollow interior of its obturator shaft, e.g., if the distal tip of the endoscope is located and maintained within the hollow interior of the clear distal tip. If the endoscope is retracted from this position, visualization is almost entirely lost since the distal tip of the endoscope, which contains all of the visualization components, is located within the opaque obturator shaft. In contrast, the optical obturator of the present invention, in accordance with various embodiments thereof, may be made entirely from transparent, or otherwise light transmissible material. By fabricating the optical obturator of the present invention entirely, or in some embodiments nearly entirely, from transparent or translucent material, an endoscope may still be able to provide visualization of the tissue irrespective of its position along the hollow interior of the obturator shaft.

In addition, a conventional optical obturator that includes a complex endoscope locking mechanisms for retaining an endoscope within the obturator shaft may be more prone to failure than the endoscope retention mechanism of various embodiments of the present invention. For example, and as mentioned above, conventional obturator assemblies often include a camming mechanism which a user may selectively rotate in order to lock an endoscope within the obturator. Such a camming mechanism requires a user to actively actuate the mechanism after an endoscope has been inserted therein. If a user forgets or otherwise neglects to actuate the camming mechanism, an endoscope that is inserted into the obturator assembly may not be sufficiently retained therewithin. The consequences of this may be serious. For example, if the user is holding the endoscope at the time, the trocar assembly may slide off of the end of the endoscope and fall to the floor—such an event would require a new trocar assembly to be employed, since the trocar assembly would no longer be sterile. Alternatively, if the user is holding the trocar assembly at the time, the endoscope may slide out of the trocar assembly and fall to the floor. Not only would the endoscope be rendered unsterile, but perhaps more significantly, the endoscope could break, resulting in costly damage to a very expensive piece of equipment. In contrast, the optical obturator of the present invention, in accordance with various embodiments thereof, may provide passive retention of the endoscope. For example, the endoscope retention mechanism, in accordance with various embodiments of the present invention, may include a structure that extends radially inwardly into the opening of the obturator housing. Such a structure may include one or more fingers that are co-molded with the obturator housing. The one or more fingers may be resiliently arranged circumferentially about the opening such that an endoscope inserted into the opening radially displaces the one or more fingers from a resting position of the one or more fingers. The one or more fingers may provide a radially force on an endoscope inserted into the opening so as to help maintain the endoscope within the hollow interior of the obturator shaft. As such, the user need not actuate any mechanism in order to retain the endoscope within the obturator—rather, the endoscope retention mechanism of the optical obturator of the present invention, in accordance with various embodiments thereof, may automatically retain an endoscope within the hollow interior of the obturator shaft and thereby eliminate, or at least reduce, the likelihood of either the trocar assembly or the endoscope falling to the floor. The same benefit is achieved by use of an endoscope retention mechanism that includes an o-ring, since the o-ring provides passive retention of the endoscope without the need for a user to actuate it.

Still another potential drawback of conventional optical obturators that include a complex endoscope locking mechanisms for retaining an endoscope within the obturator shaft may be that, because the user may forget or otherwise neglect to actuate the endoscope locking mechanism, there is an increased likelihood that the endoscope may move within the obturator assembly and thereby negatively impact the visualization of the tissue. For example, if an endoscope is allowed to inadvertently slide within a conventional obturator, the user's visualization may be lost or at least reduced, particularly if the distal tip of the endoscope, which contains all of the visualization components, is allowed to slide out of the hollow interior of the distal tip of the obturator and into the opaque obturator shaft. In contrast, the optical obturator of the present invention, in accordance with various embodiments thereof, insures that the distal tip of an endoscope will remain within the hollow interior of the penetrating member. Of course, as set forth above, even if the distal tip of the endoscope was caused to inadvertently slide out of the hollow interior of the penetrating member, the optical obturator of the present invention, in accordance with various embodiments thereof, may still provide an advantage over conventional optical obturators because, by fabricating the optical obturator of the present invention entirely from transparent or translucent material, an endoscope may still be able to provide visualization of the tissue irrespective of its position along the hollow interior of the obturator shaft and even if it is caused to slide out of the hollow interior of the penetrating member.

Yet another potential drawback of conventional optical obturators may be that, because conventional optical obturators often include separate and complex latching mechanisms for attaching the obturator to the cannula assembly, these complex latching mechanisms are more prone to malfunction than the optical obturator of the present invention, in accordance with various embodiments thereof. For example, various conventional optical obturators may include latching mechanisms that are spring-loaded, whereby a spring biases an first attachment mechanism of an obturator housing, e.g., a leg, into engagement with a corresponding receiving mechanism, e.g., an opening, of a cannula housing. These spring mechanisms may be prone to failure since springs often have unpredictable use characteristics, e.g., they bend in different directions, they lose their biasing capability over time or have their biasing capability change over time as the spring is placed under load, etc. In contrast, the optical obturator of the present invention, in accordance with various embodiments thereof, may include a latch mechanism. The latch mechanism may include a pair of radially displaceable legs disposed on opposed sides of the obturator housing. Each leg may have a tooth at its distal end. Displacing the legs radially inwardly may enable selective attachment and detachment of the teeth with respective corresponding openings of the cannula assembly. By integrally forming these radially displaceable legs with the obturator housing (as well as the various other components of the optical obturator), the optical obturator of the present invention, in accordance with various embodiments thereof, provides an arrangement in which there are no separate components, such as springs or any other such components, that could malfunction and thereby negatively impact the reliability of the latching mechanism.

Still further, and as set forth above, conventional optical obturators often include separate obturator housing components. These separate obturator housing components may function to surround and/or protect the various other mechanisms of the obturator housing, e.g., an endoscope locking mechanisms, a latching mechanisms, etc. Typically, these obturator housing components consist of two molded plastic shells that are welded together at the time of assembly and/or that are welded to other components of the obturator assembly. In addition to the costs associated with assembling these separate components and making these welds, these welds may also negatively affect the function of the obturator housing, e.g., because the welds provide an area of weakness that may be more prone to breakage, because the welds may have edges that may get caught on a surgeon's glove, etc. In contrast, the optical obturator of the present invention, in accordance with various embodiments thereof, provides an arrangement which requires no separate obturator housing components, and which may therefore avoid some of these potential drawbacks of conventional optical obturators.

Except where noted otherwise, the materials utilized in the components of the presently disclosed trocar assembly generally include materials such as, for example, ABS, polycarbonate, and any other suitable polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. An obturator for penetrating tissue, the obturator comprising:
   an obturator shaft having proximal and distal ends, the proximal end defining an opening configured for receiving an endoscope and the distal end having a tip configured to penetrate tissue, the obturator shaft having a shaft wall that defines a pair of slots disposed on opposite sides of the shaft wall, the slots extending from an outer surface of the shaft wall to an inner surface of the shaft wall, the slots being located distally of the proximal end of the obturator; and
   an elastomeric endoscope retention mechanism being mounted on the outer surface of the obturator shaft, at least a portion of the elastomeric endoscope retention mechanism extending radially inwardly through the slots of the obturator shaft so as to engage and assist retention of an endoscope inserted through the opening.

2. The obturator according to claim 1, wherein the elastomeric endoscope retention mechanism is an o-ring.

3. The obturator according to claim 2, wherein insertion of the endoscope into the opening of the obturator shaft displaces the o-ring radially from a resting position such that the o-ring provides a radially inward force on the endoscope.

4. The obturator according to claim 3, wherein the radially inward force on the endoscope maintains a position of the endoscope within the obturator shaft.

5. The obturator according to claim 1, wherein the obturator shaft includes an attachment mechanism located distally of the proximal end of the obturator.

6. The obturator according to claim 5, wherein the attachment mechanism is a latch mechanism.

7. The obturator according to claim 6, wherein the latch mechanism includes a pair of radially displaceable legs disposed on opposed sides of the obturator shaft, each leg having a tooth at its distal end.

8. A trocar assembly for penetrating tissue, the trocar assembly comprising:
- a cannula assembly including a cannula housing and a cannula sleeve extending distally from the cannula housing; and
- an obturator for penetrating tissue and being at least partially positionable within the cannula assembly, the obturator comprising:
- an obturator shaft having opposed proximal and distal ends, the proximal end having an opening configured for receiving an endoscope, the distal end including a tip configured to penetrate tissue, the obturator shaft having a shaft wall that defines a pair of slots disposed on opposite sides of the shaft wall extending therethrough, the slots being located distally of the proximal end of the obturator; and
- an endoscope retention mechanism configured to extend through the slots of the obturator shaft while engaging at least a portion of an exterior surface of the obturator shaft.

9. The trocar assembly according to claim 8, wherein the endoscope retention mechanism is an elastomeric o-ring.

10. The trocar assembly according to claim 9, wherein an endoscope inserted into the opening of the obturator shaft radially displaces the o-ring from a resting position causing the o-ring to provide a radially inward force on the endoscope.

11. The trocar assembly according to claim 10, wherein the radially inward force on the endoscope enables the o-ring to maintain a position of the endoscope with respect to the obturator shaft.

12. The trocar assembly according to claim 8, wherein the obturator shaft includes an attachment mechanism located distally of the proximal end of the obturator.

13. The trocar assembly according to claim 12, wherein the attachment mechanism is a latch mechanism including a pair of radially displaceable legs disposed on opposed sides of the obturator shaft, each leg having a tooth at its distal end.

* * * * *